United States Patent
Mayer et al.

(10) Patent No.: US 9,790,507 B2
(45) Date of Patent: Oct. 17, 2017

(54) APTAMERS AND USE OF THE APTAMERS IN THE DIAGNOSIS AND TREATMENT OF CANCER

(71) Applicant: RHEINISCHE FRIEDRICH-WILHELMS UNIVERSITÄT BONN, Bonn (DE)

(72) Inventors: Günter Mayer, Bonn (DE); Ursula Maria Katia Schöler, Troisdorf (DE); Mohammad Seyed Taghdisi Heidarian, Maschhad (IR)

(73) Assignee: RHEINISCHE FRIEDRICH-WILHELMS UNIVERSITÄT BONN (DE)

( * ) Notice: Subject to any disclaimer, the term of this patent is extended or adjusted under 35 U.S.C. 154(b) by 0 days.

(21) Appl. No.: 14/889,232

(22) PCT Filed: May 26, 2014

(86) PCT No.: PCT/EP2014/060846
§ 371 (c)(1),
(2) Date: Nov. 5, 2015

(87) PCT Pub. No.: WO2014/191359
PCT Pub. Date: Dec. 4, 2014

(65) Prior Publication Data
US 2016/0152981 A1 Jun. 2, 2016

(30) Foreign Application Priority Data
May 28, 2013 (EP) .................................. 13169493

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/115* | (2010.01) | |
| *G01N 33/53* | (2006.01) | |
| *G01N 33/574* | (2006.01) | |
| *C12Q 1/68* | (2006.01) | |
| *A61K 31/711* | (2006.01) | |
| *A61K 31/713* | (2006.01) | |

(52) U.S. Cl.
CPC .......... *C12N 15/115* (2013.01); *A61K 31/711* (2013.01); *A61K 31/713* (2013.01); *C12Q 1/6886* (2013.01); *G01N 33/5308* (2013.01); *G01N 33/57411* (2013.01); *G01N 33/57415* (2013.01); *G01N 33/57423* (2013.01); *C12N 2310/16* (2013.01); *C12N 2320/13* (2013.01); *C12Q 2525/205* (2013.01)

(58) Field of Classification Search
CPC .... C12N 15/113; C12N 2310/11; A61K 48/00
See application file for complete search history.

(56) References Cited

PUBLICATIONS

Kejing Zhang, et al. "A Novel Aptamer Developed for Breast Cancer Cell Internalization" Chem Med Chem, vol. 7, No. 1, Jan. 2, 2012. pp. 79-84.
Shoji Ohuchi "Cell-SELEX Technology" Biosearch Open Access, vol. 1, No. 6, Dec. 1, 2012. pp. 265-272.
Dastjerdi Kazem, et al. "Generation of an enriched pool of DNA aptamers for an HER2-overexpressing cell line selected by Cell SELEX" Biotechnology and Applied Biochemistry, vol. 58, No. 4, Jul. 2011. pp. 226-230.
Wei Sun, et al, "Advances and Perspectives in Cell-Specific Aptamers" Current Pharmaceutical Design, vol. 17, No. 1, Jan. 1, 2011. pp. 80-91.
Takao Kunii, et al. "Selection of DNA aptamers recognizing small cell lung cancer using living cell-SELEX", The Analyst, vol. 136, No. 7, Apr. 1, 2011, pp. 1310-1312.
Dezhi Kang, et al. "Selection of DNA Aptamers against Glioblastoma Cells with High Affinity and Specificity" Plos One, vol. 7, No. 10, Oct. 2, 2012. pp. e42731.
International Search Report issued in corresponding International Application No. PCT/EP2014/060846,. Dated Oct. 21, 2014.

*Primary Examiner* — Amy Bowman
(74) *Attorney, Agent, or Firm* — Davidson, Davidson & Kappel, LLC

(57) ABSTRACT

The present invention relates to an aptamer comprising a nucleotide sequence SEQ ID NO: 1, a composition comprising an aptamer, and the use of the aptamer in the diagnosis and treatment of cancer, particularly solid tumors.

13 Claims, 5 Drawing Sheets a)

b)

SEQUENCE LISTING

```
<160> NUMBER OF SEQ ID NOS: 34

<210> SEQ ID NO 1
<211> LENGTH: 80
<212> TYPE: DNA
<213> ORGANISM: Artificial Sequence
<220> FEATURE:
<223> OTHER INFORMATION: aptamer
<220> FEATURE:
<221> NAME/KEY: misc_feature
<222> LOCATION: (19)..(61)
<223> OTHER INFORMATION: n is a, c, g, or t

<400> SEQUENCE: 1
gctgtgtgac tcctgcaann nnnnnnnnnn nnnnnnnnnn nnnnnnnnnn nnnnnnnnnn    60
ngcagctgta tcttgtctcc                                                80

<210> SEQ ID NO 2
<211> LENGTH: 43
<212> TYPE: DNA
<213> ORGANISM: Artificial Sequence
<220> FEATURE:
<223> OTHER INFORMATION: aptamer

<400> SEQUENCE: 2
ccggactgca gagaccgtct gtcggtgaac actattagac gcg                       43

<210> SEQ ID NO 3
<211> LENGTH: 43
<212> TYPE: DNA
```

```
<213> ORGANISM: Artificial Sequence
<220> FEATURE:
<223> OTHER INFORMATION: aptamer

<400> SEQUENCE: 3
cgttgtttgt tcgctccggg ctgtagagcc tcgaagatga gtt          43

<210> SEQ ID NO 4
<211> LENGTH: 43
<212> TYPE: DNA
<213> ORGANISM: Artificial Sequence
<220> FEATURE:
<223> OTHER INFORMATION: aptamer

<400> SEQUENCE: 4
caggccggag ggactgggga ggtgcgacgt ttacgtgttc tcc          43

<210> SEQ ID NO 5
<211> LENGTH: 43
<212> TYPE: DNA
<213> ORGANISM: Artificial Sequence
<220> FEATURE:
<223> OTHER INFORMATION: aptamer

<400> SEQUENCE: 5
ccagaccgta ggggctgtct gtagaggacg ctgacgcgca cga          43

<210> SEQ ID NO 6
<211> LENGTH: 43
<212> TYPE: DNA
<213> ORGANISM: Artificial Sequence
<220> FEATURE:
<223> OTHER INFORMATION: aptamer

<400> SEQUENCE: 6
cctgttcggg cgctagcctg atagaagtgt gcgttcaatg gtg          43

<210> SEQ ID NO 7
<211> LENGTH: 43
<212> TYPE: DNA
<213> ORGANISM: Artificial Sequence
<220> FEATURE:
<223> OTHER INFORMATION: aptamer

<400> SEQUENCE: 7
caggttgggc tgatggtggg cagaccgtag ggtccgtaat ccg          43

<210> SEQ ID NO 8
<211> LENGTH: 43
<212> TYPE: DNA
<213> ORGANISM: Artificial Sequence
<220> FEATURE:
<223> OTHER INFORMATION: aptamer

<400> SEQUENCE: 8
ggcggtacgc gtgtggacag aagtgaccgc caaatagcgc ctg          43

<210> SEQ ID NO 9
<211> LENGTH: 43
<212> TYPE: DNA
<213> ORGANISM: Artificial Sequence
<220> FEATURE:
<223> OTHER INFORMATION: aptamer

<400> SEQUENCE: 9
ggggtacacg cgcatgctca tctggaccgg agggttccgg gga          43
```

<210> SEQ ID NO 10
<211> LENGTH: 43
<212> TYPE: DNA
<213> ORGANISM: Artificial Sequence
<220> FEATURE:
<223> OTHER INFORMATION: aptamer

<400> SEQUENCE: 10
caaagggtcg gcggactgtt gagaccaccg gcagcggggc att          43

<210> SEQ ID NO 11
<211> LENGTH: 43
<212> TYPE: DNA
<213> ORGANISM: Artificial Sequence
<220> FEATURE:
<223> OTHER INFORMATION: aptamer

<400> SEQUENCE: 11
gggtacggca ttgatttgct gccttattgg tgttggtggg ggg          43

<210> SEQ ID NO 12
<211> LENGTH: 43
<212> TYPE: DNA
<213> ORGANISM: Artificial Sequence
<220> FEATURE:
<223> OTHER INFORMATION: aptamer

<400> SEQUENCE: 12
catgctttat gtaacaggcg gaggccgtcc gtggtacagg ttc          43

<210> SEQ ID NO 13
<211> LENGTH: 43
<212> TYPE: DNA
<213> ORGANISM: Artificial Sequence
<220> FEATURE:
<223> OTHER INFORMATION: aptamer

<400> SEQUENCE: 13 ggagggatc acaccgtata gactgcagag ttctgtcggt gtg           43

<210> SEQ ID NO 14
<211> LENGTH: 80
<212> TYPE: DNA
<213> ORGANISM: Artificial Sequence
<220> FEATURE:
<223> OTHER INFORMATION: aptamer

<400> SEQUENCE: 14
gctgtgtgac tcctgcaaca ggccggaggg actgggagg tgcgacgttt acgtgttctc    60
cgcagctgta tcttgtctcc                                               80

<210> SEQ ID NO 15
<211> LENGTH: 80
<212> TYPE: DNA
<213> ORGANISM: Artificial Sequence
<220> FEATURE:
<223> OTHER INFORMATION: aptamer

<400> SEQUENCE: 15
gctgtgtgac tcctgcaacg ttgtttgttc gctccgggct gtagagcctc gaagatgagt    60
tgcagctgta tcttgtctcc                                                80

<210> SEQ ID NO 16

```
<211> LENGTH: 80
<212> TYPE: DNA
<213> ORGANISM: Artificial Sequence
<220> FEATURE:
<223> OTHER INFORMATION: aptamer

<400> SEQUENCE: 16
gctgtgtgac tcctgcaacc ggactgcaga gaccgtctgt cggtgaacac tattagacgc       60
ggcagctgta tcttgtctcc                                                   80

<210> SEQ ID NO 17
<211> LENGTH: 80
<212> TYPE: DNA
<213> ORGANISM: Artificial Sequence
<220> FEATURE:
<223> OTHER INFORMATION: aptamer

<400> SEQUENCE: 17
gctgtgtgac tcctgcaagg cggtacgcgt gtggacagaa gtgaccgcca aatagcgcct       60
ggcagctgta tcttgtctcc                                                   80

<210> SEQ ID NO 18
<211> LENGTH: 80
<212> TYPE: DNA
<213> ORGANISM: Artificial Sequence
<220> FEATURE:
<223> OTHER INFORMATION: aptamer

<400> SEQUENCE: 18
gctgtgtgac tcctgcaacc agaccgtagg ggctgtctgt agaggacgct gacgcgcacg       60
agcagctgta tcttgtctcc                                                   80

<210> SEQ ID NO 19
<211> LENGTH: 80
<212> TYPE: DNA
<213> ORGANISM: Artificial Sequence
<220> FEATURE:
<223> OTHER INFORMATION: aptamer

<400> SEQUENCE: 19
gctgtgtgac tcctgcaacc tgttcgggcg ctagcctgat agaagtgtgc gttcaatggt       60
ggcagctgta tcttgtctcc                                                   80

<210> SEQ ID NO 20
<211> LENGTH: 80
<212> TYPE: DNA
<213> ORGANISM: Artificial Sequence
<220> FEATURE:
<223> OTHER INFORMATION: aptamer

<400> SEQUENCE: 20
gctgtgtgac tcctgcaaca ggttgggctg atggtgggca gaccgtaggg tccgtaatcc       60
ggcagctgta tcttgtctcc                                                   80

<210> SEQ ID NO 21
<211> LENGTH: 80
<212> TYPE: DNA
<213> ORGANISM: Artificial Sequence
<220> FEATURE:
<223> OTHER INFORMATION: aptamer

<400> SEQUENCE: 21
gctgtgtgac tcctgcaagg ggtacacgcg catgctcatc tggaccggag ggttccgggg       60
```
agcagctgta tcttgtctcc 80

<210> SEQ ID NO 22
<211> LENGTH: 80
<212> TYPE: DNA
<213> ORGANISM: Artificial Sequence
<220> FEATURE:
<223> OTHER INFORMATION: aptamer

<400> SEQUENCE: 22
gctgtgtgac tcctgcaaca aagggtcggc ggactgttga gaccaccggc agcggggcat 60
tgcagctgta tcttgtctcc 80

<210> SEQ ID NO 23
<211> LENGTH: 80
<212> TYPE: DNA
<213> ORGANISM: Artificial Sequence
<220> FEATURE:
<223> OTHER INFORMATION: aptamer

<400> SEQUENCE: 23
gctgtgtgac tcctgcaagg gtacggcatt gatttgctgc cttattggtg ttggtggggg 60
ggcagctgta tcttgtctcc 80

<210> SEQ ID NO 24
<211> LENGTH: 80
<212> TYPE: DNA
<213> ORGANISM: Artificial Sequence
<220> FEATURE:
<223> OTHER INFORMATION: aptamer

<400> SEQUENCE: 24
gctgtgtgac tcctgcaaca tgctttatgt aacaggcgga ggccgtccgt ggtacaggtt 60
cgcagctgta tcttgtctcc 80

<210> SEQ ID NO 25
<211> LENGTH: 80
<212> TYPE: DNA
<213> ORGANISM: Artificial Sequence
<220> FEATURE:
<223> OTHER INFORMATION: aptamer

<400> SEQUENCE: 25
gctgtgtgac tcctgcaagg agggatcac accgtataga ctgcagagtt ctgtcggtgt 60
ggcagctgta tcttgtctcc 80

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
ggagacaaga tacagctgc 19

<210> SEQ ID NO 27
<211> LENGTH: 18
<212> TYPE: DNA
<213> ORGANISM: Artificial Sequence
<220> FEATURE:
<223> OTHER INFORMATION: primer

```
<400> SEQUENCE: 27
gctgtgtgac tcctgcaa                                                          18

<210> SEQ ID NO 28
<211> LENGTH: 80
<212> TYPE: DNA
<213> ORGANISM: Artificial Sequence
<220> FEATURE:
<223> OTHER INFORMATION: control sequence

<400> SEQUENCE: 28
gctgtgtgac tcctgcaaga cggaccagag ggcggagagc tttggcagct ctcggcatca           60
agcagctgta tcttgtctcc                                                        80

<210> SEQ ID NO 29
<211> LENGTH: 21
<212> TYPE: RNA
<213> ORGANISM: Artificial Sequence
<220> FEATURE:
<223> OTHER INFORMATION: siRNA sense

<400> SEQUENCE: 29
gaagaugcuu ggaaggaaau u                                                      21

<210> SEQ ID NO 30
<211> LENGTH: 21
<212> TYPE: RNA
<213> ORGANISM: Artificial Sequence
<220> FEATURE:
<223> OTHER INFORMATION: siRNA antisense

<400> SEQUENCE: 30
uucuucuacg aaccuuccuu u                                                      21

<210> SEQ ID NO 31
<211> LENGTH: 21
<212> TYPE: RNA
<213> ORGANISM: Artificial Sequence
<220> FEATURE:
<223> OTHER INFORMATION: siRNA sense

<400> SEQUENCE: 31
gcaaauagca uaagagcaau u                                                      21

<210> SEQ ID NO 32
<211> LENGTH: 21
<212> TYPE: RNA
<213> ORGANISM: Artificial Sequence
<220> FEATURE:
<223> OTHER INFORMATION: siRNA antisense

<400> SEQUENCE: 32
uucguuuauc guauucucgu u                                                      21

<210> SEQ ID NO 33
<211> LENGTH: 19
<212> TYPE: RNA
<213> ORGANISM: Artificial Sequence
<220> FEATURE:
<223> OTHER INFORMATION: siRNA sense

<400> SEQUENCE: 33
uucuccgaac gugucacgu                                                         19
```

```
<210> SEQ ID NO 34
<211> LENGTH: 19
<212> TYPE: RNA
<213> ORGANISM: Artificial Sequence
<220> FEATURE:
<223> OTHER INFORMATION: siRNA antisense

<400> SEQUENCE: 34
acgugacacg uucggagaa                                              19
```

APTAMERS AND USE OF THE APTAMERS IN THE DIAGNOSIS AND TREATMENT OF CANCER

Figure 1:
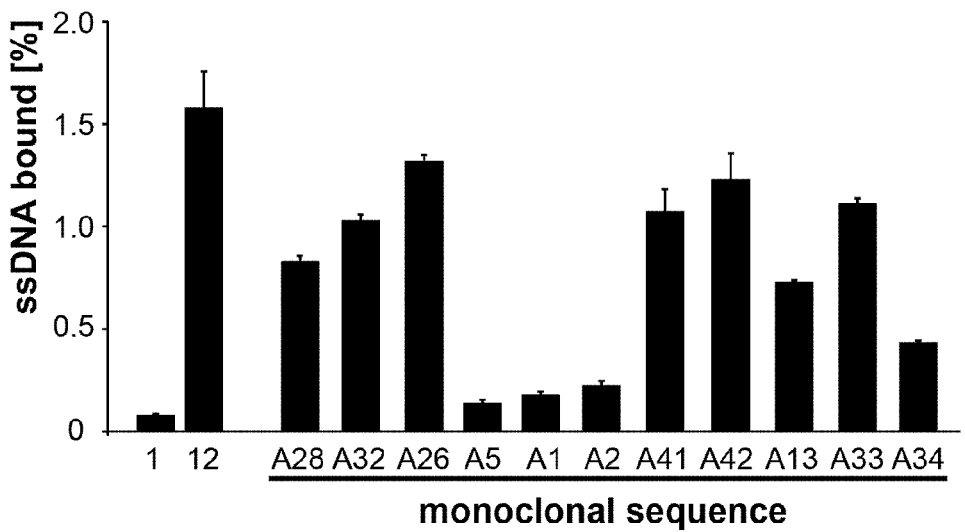
Figure 1:
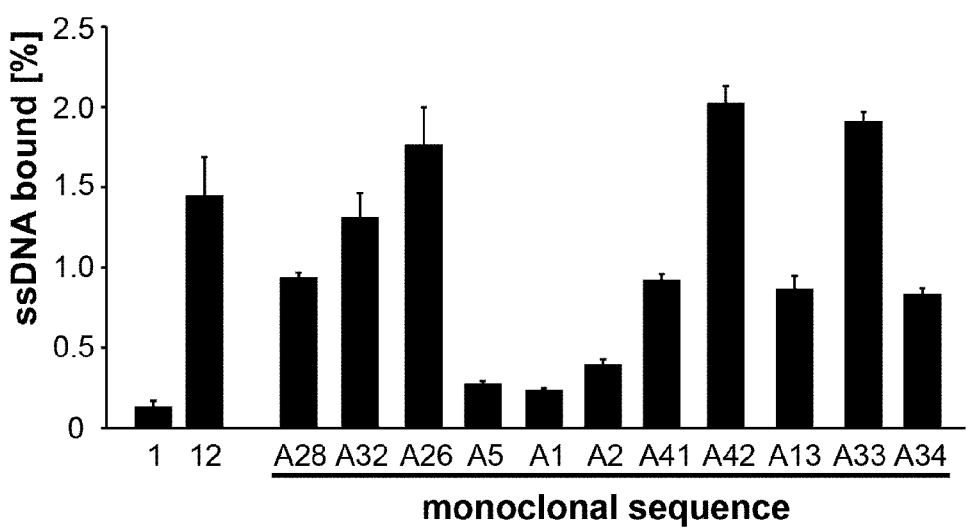

This application is a U.S. national phase application under 35 U.S.C. §371 of International Application No. PCT/EP2014/060846, filed May 26, 2014, which claims priority to European Application No. 13169493.7, filed May 28, 2013; the disclosures of which are all hereby incorporated by reference herein.

Cancer is a leading cause of death worldwide, and the development of novel diagnostic and therapeutic regimens is still mandatory. A significant fraction of the overall improvement in cancer outcome is attributed to early diagnosis, which requires sophisticated molecular probes and biomarkers. Further, tumour therapies are not always successful and mistreatment causes high costs. Biomarker diagnostic improves the determination and therapeutic treatment of tumours. Nonetheless, only very few biomarkers are available for effective cancer diagnosis. The current standard cancer treatment, the use of chemotherapeutics for tumour patient treatment frequently results in the manifestation of severe side effects. Targeted therapy has become a promising alternative within the last decade, since targeted therapy provides reduced toxicity, due to reduced level of therapeutics needed. For targeted therapy, molecules that selectively recognize a distinct cell-surface receptor are utilized to transport their cargos such as chemotherapeutics or other regimens to the proximity and into pathogenic cells. Antibodies have been used for these issues but their applicability is limited. Despite certain progress that has been achieved within the past decade, their site-directed modification is still challenging. Moreover, antibodies raise unwanted immunogenic responses, which may result in severe side effects upon in vivo administration.

Further development of targeted approaches for the specific delivery of therapeutically active substances is urgently required. Especially the targeted delivery of macromolecular charged drug-like molecules, for example antagomirs and siRNA, is limited since these candidates do not cross cell membranes but rather have to be actively provided to the intracellular milieu.

The so-called aptamers that are short single-stranded nucleic acid molecules, which can fold into defined three-dimensional structures and recognize specific target structures, have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumour cell lines have been identified. Amongst them are specific aptamers for leukemia, liver cancer, small cell lung cancer, ovarian cancer, and colon cancer cells, and some of them have been proven to be promising tools for diagnosis but also for the targeted delivery of potential drugs.

Therefore, the object underlying the present invention was to provide aptamers that recognize tumour cells.

The problem is solved by an aptamer, wherein the aptamer comprises a nucleotide sequence (SEQ ID NO: 1) according to general formula (1) as given as follows or a pharmaceutically acceptable salt thereof:

5'-GCTGTGTGACTCCTGCAA-$N_{43}$-GCAGCTG-TATCTTGTCTCC-3' (1) (SEQ ID NO: 1), wherein:

$N_{43}$ is a nucleotide sequence selected from the group comprising:

5'-CCGGACTGCAGAGACCGTCTGTCGGT-GAACACTATTAGACGCG-3' (SEQ ID NO: 2),
5'-CGTTGTTTGTTCGCTCCGGGCTGTAGAGCCTC-GAAGATGAGTT-3' (SEQ ID NO: 3),
5'-CAGGCCGGAGGGACTGGGGAGGTGCGACGTT-TACGTGTTCTCC-3' (SEQ ID NO: 4),
5'-CCAGACCGTAGGGGCTGTCTGTAGAG-GACGCTGACGCGCACGA-3' (SEQ ID NO: 5),
5'-CCTGTTCGGGCGCTAGCCTGATAGAAGTGT-GCGTTCAATGGTG-3' (SEQ ID NO: 6),
5'-CAGGTTGGGCTGATGGTGGGCAGACCG-TAGGGTCCGTAATCCG-3' (SEQ ID NO: 7),
5'-GGCGGTACGCGTGTGGACAGAAGTGACCGC-CAAATAGCGCCTG-3' (SEQ ID NO: 8),
5'-GGGGTACACGCGCATGCTCATCTGGACCG-GAGGGTTCCGGGGA-3' (SEQ ID NO: 9),
5'-CAAAGGGTCGGCGGACTGTTGAGACCACCG-GCAGCGGGGCATT-3' (SEQ ID NO: 10),
5'-GGGTACGGCATTGATTTGCTGCCTTATTGGTGT-TGGTGGGGGG-3' (SEQ ID NO: 11),
5'-CATGCTTTATGTAACAGGCGGAGGCCGTC-CGTGGTACAGGTTC-3' (SEQ ID NO: 12) and
5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof.

Surprisingly, DNA aptamers could be selected that reveal broad-spectrum recognition properties for various cancer cells particularly those derived from solid tumours, while non-tumourgenic and primary healthy cells are not recognized. Further, the aptamers do not interact with soluble tumour derived cells. The aspect that the identified aptamers recognise not only a specific tumour sub-type but rather interact with a series of tumours renders the aptamers applicable as so-called broad-spectrum diagnostics and therapeutics. Advantageously, this enables the treatment of several tumour types with one formulation. The broad applicability of one aptamer towards several tumours significantly reduces the developing costs for pharmaceuticals using the same. Further, investigation of cell-binding behaviour with flow cytometry showed that the aptamers revealed very good apparent affinities in the nanomolar range.

The aptamers are useful for diagnostic and therapeutic purposes. Further, it could be shown that some of the aptamers are taken up by tumour cells and thus can function as molecular vehicles for the targeted delivery of anti-cancer agents such as siRNA into tumour cells.

As used herein, the term "aptamer" refers to a small single-stranded oligonucleotide that recognises its target with high specificity and binds to the target with high affinity.

If not stated otherwise, the term "nucleotide" refers to a ribonucleotide or a deoxyribonucleotide. The aptamer according to the invention hence can be provided in the form of a single-stranded DNA or RNA molecule. As will be obvious to a person of ordinary skills in the art, if the nucleic acid is an RNA molecule the thymidine or "T" in the nucleotide sequence is to be read as meaning "U" or uridine. Preferably, the aptamer comprises a deoxyribonucleotide sequence. DNA aptamers can exhibit better stability. Further, the nucleotides may comprise a chemical modification such as a locked nucleic acid (LNA). Preferred substituents are selected from the group comprising fluorine, $C_1$-$C_5$-alkoxy particularly methoxy, or an amino group.

It is assumed that even if the nucleotide sequence of the aptamer comprises an addition, deletion or substitution of one or several nucleotides it will continue to show the broad-spectrum recognition properties towards solid tumour. For example, the aptamer may preserve its recognition properties albeit portions of the 5'- and/or the 3'-terminal sequence of SEQ ID NO: 1 according to the invention are deleted. So, aptamers comprising a nucleotide sequence of SEQ ID NOs: 2 to 13 and a portion of the 5'-terminus and/or a portion of the 3'-terminus may preserve their recognition properties. Further, aptamers comprising a nucleotide sequence of SEQ ID NOs: 2 to 13 and the 5'- or the 3'-terminus of SEQ ID NO: 1 may preserve their recognition properties. Hence, also aptamers comprising a nucleotide sequence selected from the group comprising SEQ ID NOs: 2 to 13, particularly aptamers comprising a nucleotide sequence selected from the group comprising SEQ ID NOs: 2 to 13 and the 5'- or the 3'-terminal sequence of SEQ ID NO: 1 or portions thereof, as well as pharmaceutically acceptable salts thereof are part of the present invention.

As used herein, the term "broad-spectrum" applicability refers to aptamers that recognise tumour cells and tumours of different origin. Advantageously, the aptamers recognise different solid tumours but do not interact with healthy cells such as endothelial cells and tissue.

The inventors have made considerable efforts to identify an aptamer that exhibits broad-spectrum applicability for solid tumours. Such an aptamer can be used for cancer diagnostics and therapeutics of multiple tumours.

Aptamers can be selected against complex targets such as cells and tissues, using the cell-SELEX (Systematic Evolution of Ligands by Exponential enrichment) technique. The cell-SELEX technique allows the development of aptamers for diseased cells even when surface marker targets are unknown. A human mammary gland adenocarcinoma cell line (MCF-7) was used as complex target during the whole cell-SELEX. To deprive common cell-recognizing nucleic acid motifs a human lung carcinoma cell line, namely H460, was chosen. In this way the nucleic acids recognizing common cell structures could be eliminated, though limited to the extent possible. As a result, the inventors have selected aptamers, which reveal broad-spectrum recognition properties to solid tumour cancer cells without binding to healthy cells or interaction with soluble tumour derived cells.

In contrast to employing highly specific aptamers for targeting a single tumour type, aptamers with broad-spectrum applicability referring to aptamers that recognising tumour cells and tumours of different origin, but which do not interact with healthy cells and tissue, may be employed for the diagnosis and treatment of various tumours.

The aptamer comprises a nucleotide sequence of SEQ ID NO: 1, wherein $N_{43}$ is a sequence of 43 nucleotides selected from the group comprising or consisting of SEQ ID NOs: 2 to 13. Preferably, the aptamer comprises a nucleotide sequence of SEQ ID NO: 1, wherein $N_{43}$ is a sequence selected from the group comprising or consisting of SEQ ID NOs: 2 to 10. Advantageously, aptamers comprising SEQ ID NOs: 2 to 10 revealed higher binding to MCF-7 and H460 cells.

The aptamer may have a nucleotide sequence selected from the group comprising or consisting of SEQ ID NOs: 14 to 25. In an embodiment, the nucleotide sequence is selected from the group comprising:

```
                                            (SEQ ID NO: 14)
5'-GCTGTGTGACTCCTGCAACAGGCCGGAGGGACTGGGGAGGT

GCGACGTTTACGTGTTCTCCGCAGCTGTATCTTGTCTCC-3', (SEQ ID NO: 15)
5'-GCTGTGTGACTCCTGCAACGTTGTTTGTTCGCTCCGGGCTG

TAGAGCCTCGAAGATGAGTTGCAGCTGTATCTTGTCTCC-3', (SEQ ID NO: 16)
5'-GCTGTGTGACTCCTGCAACCGGACTGCAGAGACCGTCTGTC

GGTGAACACTATTAGACGCGGCAGCTGTATCTTGTCTCC-3',
and (SEQ ID NO: 17)
5'-GCTGTGTGACTCCTGCAAGGCGGTACGCGTGTGGACAGAAG

TGACCGCCAAATAGCGCCTGGCAGCTGTATCTTGTCTCC-3'.
```

Advantageously, the aptamers comprising SEQ ID NOs: 14 to 17 showed particularly strong recognition of cancer cells compared to non-cancer cells and/or can enter cancer cells upon recognition.

Preferably, the nucleotide sequence is selected from the group comprising SEQ ID NO: 14 (A28), SEQ ID NO: 15 (A32), and SEQ ID NO: 16 (A26). Advantageously, the aptamers comprising SEQ ID NOs: 14, 15 and 16 own a very good specificity towards solid-tumour derived cancer cells. It was found that the aptamers showed strong binding to cells derived from breast cancer, lung cancer, pancreatic cancer, and cervix cancer cell lines, while the aptamers showed no significant interaction with blood tumour cell lines, primary cells from healthy individuals and human umbilical vain endothelial cells.

In a further embodiment, the aptamer comprises the nucleotide sequence SEQ ID NO: 16 (A26) or SEQ ID NO: 17 (A33). Advantageously, the aptamers of sequence SEQ ID NO: 16 (A26) and SEQ ID NO: 17 (A33) could be shown to enter solid cancer cells upon recognition. Without being bound to a specific theory, it is assumed that the aptamers enter the cells. It could be shown that the aptamers were clearly localized inside the tumour cells of human mammary gland adenocarcinoma cell line (MCF-7) after incubation. These results qualify particularly the aptamers of sequence SEQ ID NO: 16 (A26) and SEQ ID NO: 17 (A33) as molecular vehicles for cargo delivery into tumour cells. Hence, in a further embodiment, the aptamer comprises the nucleotide sequence SEQ ID NO: 17 (A33). Advantageously, the aptamer qualifies to be useful as molecular vehicle for intracellular delivery of cargo into tumour cells.

In a most preferred embodiment, the aptamer comprises the nucleotide sequence SEQ ID NO: 16 (A26). It could be shown that complexes of the aptamer of sequence SEQ ID NO: 16 (A26) and different siRNA molecules can enter solid-tumour cells and reduce tumour cell viability. Advantageously, the aptamer of sequence SEQ ID NO: 16 (A26) can combine a very good specificity towards solid-tumour cancer cells with the ability to function as molecular vehicle for transport of cargo anti-cancer agents into tumour cells.

A further aspect of the present invention relates to an aptamer comprising a nucleotide sequence (SEQ ID NO: 1)

according to general formula (1) as given as follows or a pharmaceutically acceptable salt thereof:

5'-GCTGTGTGACTCCTGCAA-N$_{43}$-GCAGCTG-TATCTTGTCTCC-3' (1) (SEQ ID NO: 1), wherein N$_{43}$ is a nucleotide sequence selected from the group comprising:

5'-CCGGACTGCAGAGACCGTCTGTCGGT-GAACACTATTAGACGCG-3' (SEQ ID NO: 2),

5'-CGTTGTTTGTTCGCTCCGGGCTGTAGAGCCTC-GAAGATGAGTT-3' (SEQ ID NO: 3),

5'-CAGGCCGGAGGGACTGGGGAGGTGCGACGTT-TACGTGTTCTCC-3' (SEQ ID NO: 4),

5'-CCAGACCGTAGGGGCTGTCTGTAGAG-GACGCTGACGCGCACGA-3' (SEQ ID NO: 5),

5'-CCTGTTCGGGCGCTAGCCTGATAGAAGTGT-GCGTTCAATGGTG-3' (SEQ ID NO: 6),

5'-CAGGTTGGGCTGATGGTGGGCAGACCG-TAGGGTCCGTAATCCG-3' (SEQ ID NO: 7),

5'-GGCGGTACGCGTGTGGACAGAAGTGACCGC-CAAATAGCGCCTG-3' (SEQ ID NO: 8),

5'-GGGGTACACGCGCATGCTCATCTGGACCG-GAGGGTTCCGGGGA-3' (SEQ ID NO: 9),

5'-CAAAGGGTCGGCGGACTGTTGAGACCACCG-GCAGCGGGGCATT-3' (SEQ ID NO: 10),

5'-GGGTACGGCATTGATTTGCTGCCTTATTGGTGT-TGGTGGGGGG-3' (SEQ ID NO: 11),

5'-CATGCTTTATGTAACAGGCGGAGGCCGTC-CGTGGTACAGGTTC-3' (SEQ ID NO: 12) and

5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof, for use as a medicament or a diagnostic reagent.

The aptamer may have a nucleotide sequence selected from the group comprising or consisting of SEQ ID NOs: 14 to 25. Preferably, the aptamer comprises a nucleotide sequence of SEQ ID NO: 1, wherein N$_{43}$ is a sequence selected from the group comprising or consisting of SEQ ID NOs: 2 to 10. In an embodiment, the nucleotide sequence is selected from the group comprising SEQ ID NO: 14, SEQ ID NO: 15, SEQ ID NO: 16, and SEQ ID NO: 17. The nucleotide sequence of the aptamer can be selected from the group comprising SEQ ID NO: 14, SEQ ID NO: 15, and SEQ ID NO: 16. Further, the aptamer can comprise the nucleotide sequence SEQ ID NO: 16 or SEQ ID NO: 17. In a most preferred embodiment, the aptamer comprises the nucleotide sequence SEQ ID NO: 16.

The aptamers recognise cancer cells, particularly show specificity towards solid-tumour derived cancer cells, and/or can enter cancer cells upon recognition and qualify as molecular vehicles for cargo delivery into tumour cells. Hence, the aptamers of the present invention represent promising tools for cancer therapy and diagnosis. Preferably, the aptamers are capable of binding specifically to solid-tumour derived cancer cells. Further, the aptamers generally are suited for binding to microvesicles originating from these cancer cells.

Beneficially, the aptamers recognise not only a specific tumour sub-type but rather interact with a series of tumours, which renders the aptamers applicable as so-called broad-spectrum diagnostics and therapeutics. This facilitates the treatment of several tumour types with one formulation. Preferably, the aptamers are capable of binding specifically to solid-tumour cells of different origin. More preferably, the aptamers are capable of binding specifically to cells of at least three or four different solid-tumour types.

A further aspect of the present invention relates to an aptamer comprising a nucleotide sequence (SEQ ID NO: 1) according to general formula (1) as given as follows or a pharmaceutically acceptable salt thereof:

5'-GCTGTGTGACTCCTGCAA-N$_{43}$-GCAGCTG-TATCTTGTCTCC-3' (1) (SEQ ID NO: 1), wherein N$_{43}$ is a nucleotide sequence selected from the group comprising:

5'-CCGGACTGCAGAGACCGTCTGTCGGT-GAACACTATTAGACGCG-3' (SEQ ID NO: 2),

5'-CGTTGTTTGTTCGCTCCGGGCTGTAGAGCCTC-GAAGATGAGTT-3' (SEQ ID NO: 3),

5'-CAGGCCGGAGGGACTGGGGAGGTGCGACGTT-TACGTGTTCTCC-3' (SEQ ID NO: 4),

5'-CCAGACCGTAGGGGCTGTCTGTAGAG-GACGCTGACGCGCACGA-3' (SEQ ID NO: 5),

5'-CCTGTTCGGGCGCTAGCCTGATAGAAGTGT-GCGTTCAATGGTG-3' (SEQ ID NO: 6),

5'-CAGGTTGGGCTGATGGTGGGCAGACCG-TAGGGTCCGTAATCCG-3' (SEQ ID NO: 7),

5'-GGCGGTACGCGTGTGGACAGAAGTGACCGC-CAAATAGCGCCTG-3' (SEQ ID NO: 8),

5'-GGGGTACACGCGCATGCTCATCTGGACCG-GAGGGTTCCGGGGA-3' (SEQ ID NO: 9),

5'-CAAAGGGTCGGCGGACTGTTGAGACCACCG-GCAGCGGGGCATT-3' (SEQ ID NO: 10),

5'-GGGTACGGCATTGATTTGCTGCCTTATTGGTGT-TGGTGGGGGG-3' (SEQ ID NO: 11),

5'-CATGCTTTATGTAACAGGCGGAGGCCGTC-CGTGGTACAGGTTC-3' (SEQ ID NO: 12) and

5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof, for use in the diagnosis and treatment of cancer, particularly solid tumours.

It was found that the aptamers specifically detect and bind to cancer cells, particularly to solid tumour cells. This suggests that the aptamers according to the invention can be used for the diagnosis of cancer. Advantageously, when not recognising blood tumour cells, the aptamers particularly can be advantageously used for the diagnosis of solid tumours. Further, it was found that the aptamers upon recognition are able to enter solid cancer cells carrying siRNA molecules influencing tumour cell viability. This surprisingly suggests that the aptamers according to the invention can be advantageously used for the treatment of cancer, particularly solid tumours. Hence, the aptamers are useful as a medicament or a diagnostic reagent. Advantageously, the aptamers specifically are useful as a medicament or a diagnostic reagent for solid tumours.

As the aptamers are able to specifically enter solid tumour cells upon recognition, the aptamers may prove suitable for first line diagnosis or treatment. The term "first-line treatment" refers to the initial, or first treatment recommended for a disease or illness. Particularly, regarding the low side effects, due to the reduced amount of active substance, treatment using the aptamers as a medicament may become the standard treatment. Furthermore, the modularity at hand offers a combinational treatment using one aptamer transporting several active molecules, thereby circumventing otherwise fast occurring drug resistances.

The aptamer may have a nucleotide sequence selected from the group comprising or consisting of SEQ ID NOs: 14 to 25. Preferably, the aptamer comprises a nucleotide sequence of SEQ ID NO: 1, wherein N$_{43}$ is a sequence selected from the group comprising or consisting of SEQ ID NOs: 2 to 10. In an embodiment, the nucleotide sequence is selected from the group comprising SEQ ID NO: 14, SEQ ID NO: 15, SEQ ID NO: 16, and SEQ ID NO: 17. The nucleotide sequence of the aptamer can be selected from the group comprising SEQ ID NO: 14, SEQ ID NO: 15, and SEQ ID NO: 16. Further, the aptamer can comprise the nucleotide sequence SEQ ID NO: 16 or SEQ ID NO: 17. In a most preferred embodiment, the aptamer comprises the nucleotide sequence SEQ ID NO: 16.

As used herein, the term "solid tumour" refers to a solid mass of cancer cells that grow in organ systems and can occur anywhere in the body. The term solid tumour as used herein does not refer to blood cancers. Preferred solid tumours are selected from the group comprising mammary gland adenocarcinoma, breast cancer, lung cancer, cervix cancer and pancreas carcinoma. Advantageously, the aptamers show strong binding to cells derived from these cancer cell lines.

The aptamers according to the present invention also are usable in form of pharmaceutically acceptable salts thereof. The term "pharmaceutically acceptable salts" refers to salts prepared from pharmaceutically acceptable non-toxic bases or acids. A pharmaceutically acceptable salt can be conveniently prepared from pharmaceutically acceptable non-toxic bases, including inorganic bases and organic bases. Preferred salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines. Preferably, the pharmaceutically acceptable salt is selected from the group of sodium or potassium salts. Also, calcium or magnesium salts can be preferred.

For use as a medicament or a diagnostic reagent the aptamers can be used or included in a composition. In embodiments, the composition comprising an aptamer according to the invention is usable in the detection or diagnosis, or the treatment of cancer, particularly solid tumours. Particularly for use as a diagnostic reagent the aptamers can be used or included in a diagnostic composition. Particularly for use as a medicament the aptamers can be used or included in a pharmaceutical composition.

Accordingly, in another aspect the present invention relates to a composition comprising an aptamer according to the invention. The composition particularly is usable in the detection or diagnosis of cancer, particularly solid tumours. When the aptamer is brought into contact with a sample, it will bind specifically to a cancerous cell present in the sample. The aptamer can comprise a labelling which provides that the bound aptamer can be detected by determining the presence or absence of a signal provided by the label. For example, the aptamer can be labelled with a fluorescent dye. A fluorescence-labelling, for example provided by a fluorescence dye, can provide a visualisation of the bound aptamer by fluorescence or laser scanning microscopy or flow cytometry. Further, particularly for detection purposes, the aptamer can be immobilised on conventional supports such as beads providing a tool for the detection of aptamer-bound cancerous cells and thus diagnosing cancer. Further, the aptamer can be biotinylated or coupled to streptavidin, avidin or neutravidin for use in the specific detection of tumour cells.

Besides being useful for detecting or diagnosing cancer by recognising tumour cells, the aptamers also have shown to be applicable for targeted therapies. Accordingly, in another aspect the present invention relates to a pharmaceutical composition comprising as an active ingredient an aptamer according to the invention.

It could be shown that the aptamers are capable of facilitating the delivery of siRNA (small interfering RNA) molecules into tumour cells. Hence, the pharmaceutical composition the aptamers can particularly be useful as a molecular vehicle for delivery of cargo such as siRNA molecules into the cells leading to a deprivation of tumour cells.

As used herein, the term "siRNA" refers to so called small interfering RNA also known as short interfering RNA or silencing RNA, which are double-stranded RNA molecules. siRNA may interfere with protein translation, by binding to messenger RNA of their complementary sequence. Thereby, siRNAs prevent protein translation.

Aptamer-siRNA conjugates are usable in aptamer-targeted cell-specific RNA interference in tumour cells, for example prohibiting protein translation in vitro and in vivo. Certain siRNA molecules can inhibit the expression of genes involved in the growth and metastasis of tumour cells. For example siRNA molecules targeting Poly (A) binding protein or Ubiquitin protein ligase E3 component n-recognin 5 (UBR5), can down-regulate the expression of anti-apoptotic genes. Hence, aptamer-siRNA chimeras can induce tumour cell apoptosis. Further, other cancer-specific drugs, toxins inducing apoptosis or cell death by i.e. necrosis, or antagomirs can be attached to the aptamers to be delivered to tumour cells.

As used herein, the term "antagomir" refers to an oligonucleotide that can bind to microRNA (miRNA). Antagomirs are usable to affect the regulation of microRNA molecules or inhibit or silence endogenous microRNA. For example, antagomirs against microRNA 155 or miR21 induce a knock-down resulting in an inhibition of tumour growth.

Effector molecules can be directly coupled to the aptamer, in a covalent or non-covalent fashion. Alternatively, the aptamer can be attached to the surface of a liposome containing an anticancer agent such as a toxin, a cancer growth inhibitor gene, an antagomir or a siRNA molecule. A composition comprising an aptamer according to the invention, particularly a pharmaceutical composition for use in the treatment of cancer, particularly solid tumours, can further comprise an anti-cancer agent such as a toxin, anti-cancer growth inhibitor gene, an antagomir or siRNA for solid tumour-specific drug delivery.

Accordingly, in a further aspect the present invention relates to a solid tumour-specific drug delivery composition comprising an aptamer according to the invention, and an anti-cancer agent such as a toxin, an anti-cancer growth inhibitor gene, an antagomir, siRNA, or combinations thereof. Also, so called combined approaches using a combination of at least two of a toxin, an anti-cancer growth inhibitor gene, an antagomir, or siRNA may be used in therapy. Particularly, a combination of an antagomir and siRNA may prove useful as a combined approach. Furthermore, the modularity at hand offers a combinational treatment using an aptamer transporting several active molecules, thereby circumventing otherwise fast occurring drug resistances.

The compositions particularly the pharmaceutical composition may be produced under sterile conditions using standard pharmaceutical techniques well known to those skilled in the art. For compositions convenient pharmaceutical media may be employed. For example, water, glycols, oils, alcohols and the like may be used to form liquid preparations such as solutions. The composition may comprise a pharmaceutical carrier, which can be, for example, a solid, liquid, or gas. Suitable carriers preferably are liquid and correspond to the substances ordinarily employed in formulation technology for pharmaceutical formulations. The compositions can be suitable for parenteral administration, including subcutaneous, intramuscular, and intravenous administration. Compositions suitable for parenteral administration may be prepared as solutions or suspensions of the aptamer in water. Compositions suitable for injectable use include sterile aqueous solutions or dispersions.

The present invention also relates to the use of an aptamer comprising a nucleotide sequence (SEQ ID NO: 1) according to general formula (1) as given as follows or a pharmaceutically acceptable salt thereof:

5'-GCTGTGTGACTCCTGCAA-$N_{43}$-GCAGCTG-TATCTTGTCTCC-3' (1) (SEQ ID NO: 1), wherein $N_{43}$ is a nucleotide sequence selected from the group comprising:

5'-CCGGACTGCAGAGACCGTCTGTCGGT-GAACACTATTAGACGCG-3' (SEQ ID NO: 2),

5'-CGTTGTTTGTTCGCTCCGGGCTGTAGAGCCTC-GAAGATGAGTT-3' (SEQ ID NO: 3),

5'-CAGGCCGGAGGGACTGGGGAGGTGCGACGTT-TACGTGTTCTCC-3' (SEQ ID NO: 4),

5'-CCAGACCGTAGGGGCTGTCTGTAGAG-GACGCTGACGCGCACGA-3' (SEQ ID NO: 5),

5'-CCTGTTCGGGCGCTAGCCTGATAGAAGTGT-GCGTTCAATGGTG-3' (SEQ ID NO: 6),

5'-CAGGTTGGGCTGATGGTGGGCAGACCG-TAGGGTCCGTAATCCG-3' (SEQ ID NO: 7),

5'-GGCGGTACGCGTGTGGACAGAAGTGACCGC-CAAATAGCGCCTG-3' (SEQ ID NO: 8),

5'-GGGGTACACGCGCATGCTCATCTGGACCG-GAGGGTTCCGGGGA-3' (SEQ ID NO: 9),

5'-CAAAGGGTCGGCGGACTGTTGAGACCACCG-GCAGCGGGGCATT-3' (SEQ ID NO: 10),

5'-GGGTACGGCATTGATTTGCTGCCTTATTGGTGT-TGGTGGGGGG-3' (SEQ ID NO: 11),

5'-CATGCTTTATGTAACAGGCGGAGGCCGTC-CGTGGTACAGGTTC-3' (SEQ ID NO: 12) and

5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof, for the manufacture of a medicament or a diagnostic reagent.

The present invention particularly relates to the use of an aptamer comprising a nucleotide sequence (SEQ ID NO: 1) according to general formula (1) as given as follows or a pharmaceutically acceptable salt thereof:

5'-GCTGTGTGACTCCTGCAA-$N_{43}$-GCAGCTG-TATCTTGTCTCC-3' (1) (SEQ ID NO: 1), wherein $N_{43}$ is a nucleotide sequence selected from the group comprising:

5'-CCGGACTGCAGAGACCGTCTGTCGGT-GAACACTATTAGACGCG-3' (SEQ ID NO: 2),

5'-CGTTGTTTGTTCGCTCCGGGCTGTAGAGCCTC-GAAGATGAGTT-3' (SEQ ID NO: 3),

5'-CAGGCCGGAGGGACTGGGGAGGTGCGACGTT-TACGTGTTCTCC-3' (SEQ ID NO: 4),

5'-CCAGACCGTAGGGGCTGTCTGTAGAG-GACGCTGACGCGCACGA-3' (SEQ ID NO: 5),

5'-CCTGTTCGGGCGCTAGCCTGATAGAAGTGT-GCGTTCAATGGTG-3' (SEQ ID NO: 6),

5'-CAGGTTGGGCTGATGGTGGGCAGACCG-TAGGGTCCGTAATCCG-3' (SEQ ID NO: 7),

5'-GGCGGTACGCGTGTGGACAGAAGTGACCGC-CAAATAGCGCCTG-3' (SEQ ID NO: 8),

5'-GGGGTACACGCGCATGCTCATCTGGACCG-GAGGGTTCCGGGGA-3' (SEQ ID NO: 9),

5'-CAAAGGGTCGGCGGACTGTTGAGACCACCG-GCAGCGGGGCATT-3' (SEQ ID NO: 10),

5'-GGGTACGGCATTGATTTGCTGCCTTATTGGTGT-TGGTGGGGGG-3' (SEQ ID NO: 11),

5'-CATGCTTTATGTAACAGGCGGAGGCCGTC-CGTGGTACAGGTTC-3' (SEQ ID NO: 12) and

5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof, for the manufacture of a diagnostic reagent for the detection or diagnosis of, or a medicament for the treatment of cancer, particularly solid tumours.

The aptamer may have a nucleotide sequence selected from the group comprising or consisting of SEQ ID NOs: 14 to 25. Preferably, the aptamer comprises a nucleotide sequence of SEQ ID NO: 1, wherein $N_{43}$ is a sequence selected from the group comprising or consisting of SEQ ID NOs: 2 to 10. In an embodiment, the nucleotide sequence is selected from the group comprising SEQ ID NO: 14, SEQ ID NO: 15, SEQ ID NO: 16, and SEQ ID NO: 17. The nucleotide sequence of the aptamer can be selected from the group comprising SEQ ID NO: 14, SEQ ID NO: 15, and SEQ ID NO: 16. Further, the aptamer can comprise the nucleotide sequence SEQ ID NO: 16 or SEQ ID NO: 17. In a most preferred embodiment, the aptamer comprises the nucleotide sequence SEQ ID NO: 16.

A further aspect of the present invention relates to an in vitro method of detecting or diagnosing a predisposition of cancer or cancer, particularly solid tumours, the method comprising the step of detecting the binding of an aptamer according to the invention to a sample obtained from a subject.

As used herein, the term "sample" refers to any material, which probably contains tumour cells, including any liquid or fluid sample or solid material, particularly a sample derived from a biological source such as a patient or test subject. The term sample particularly refers to biological material, for example cells or tissues, biological fluids or supernatants. The biological material can be a tissue specimen removed from a cancer subject, preferably humans, for example, by surgical resection or biopsy. The biological material can be a body fluid such as blood, serum, plasma, saliva, phlegm and urine.

The method comprises bringing the aptamer into contact with a sample, which probably contains tumour cells, or microvesicles originating from tumour cells. The sample may be derived from a biological source such as a cancer subject. The sample for example can comprise cells or a tissue specimen isolated from a cancer subject, preferably a human, for example, by surgical resection or biopsy. The sample also can be a body fluid such as blood, serum, plasma, saliva, phlegm and urine.

A further aspect of the present invention relates to a method of treating cancer particularly solid tumours, the method comprising the step of administering to a subject a therapeutically effective amount of an aptamer or a pharmaceutical composition according to the invention. The term "therapeutically effective amount" is used herein to mean an amount or dose sufficient to cause an improvement in a clinically significant condition in the subject.

Unless otherwise defined, the technical and scientific terms used herein have the same meaning as commonly understood by one of ordinary skill in the art to which this invention belongs.

The Examples, which follow serve to illustrate the invention in more detail but do not constitute a limitation thereof.

The figures show:

FIG. 1 The screening of selected aptamers candidates against MCF-7 in FIG. 1a) and H460 in FIG. 1b) using radioactively labelled aptamers. The cells were washed and incubated with the aptamers. The amount of ssDNA bound to the cells was measured using radioactive analysis.

Figure 2:
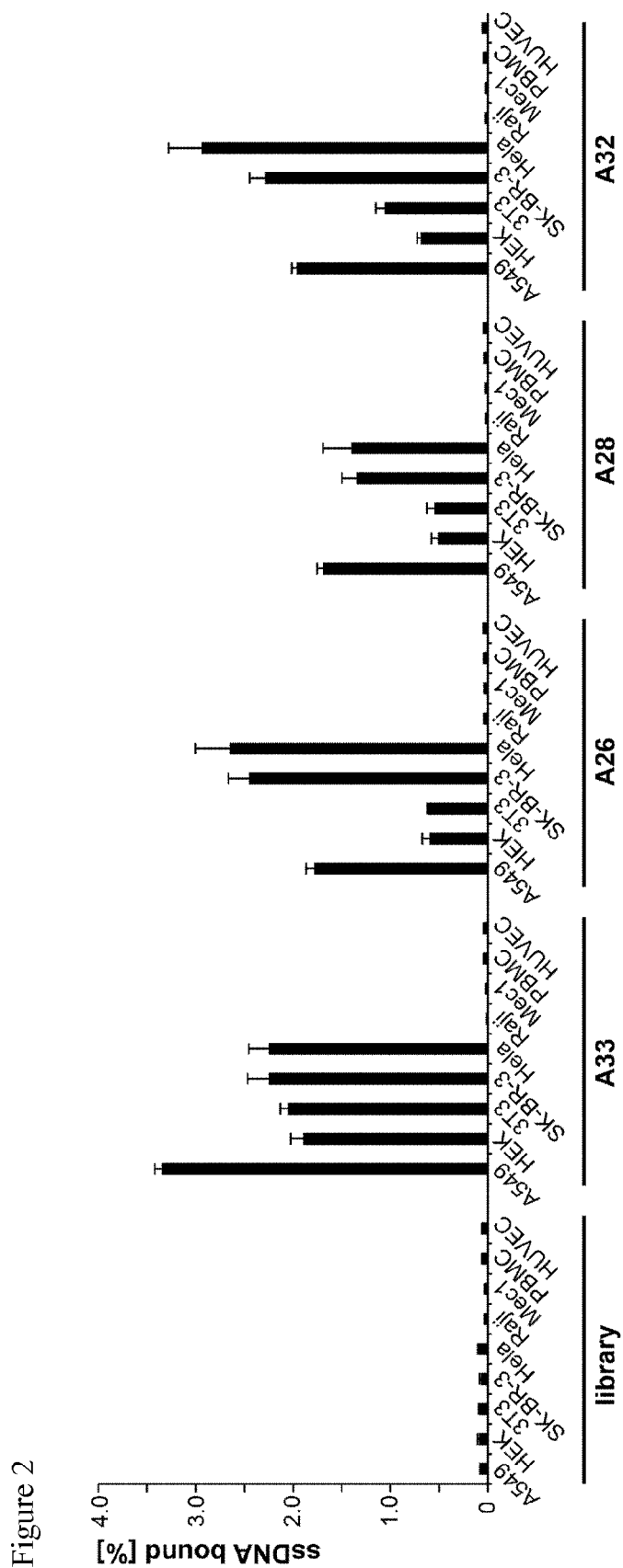

FIG. 2 A selectivity study to assess the recognition of aptamers A33, A26, A28 and A32 of different cell lines. The developed aptamers and the starting pool (library) were 5'-$^{32}$P-labeled and incubated with different cell lines. The amount of ssDNA bound to the cells was measured using radioactive analysis.

Figure 3:
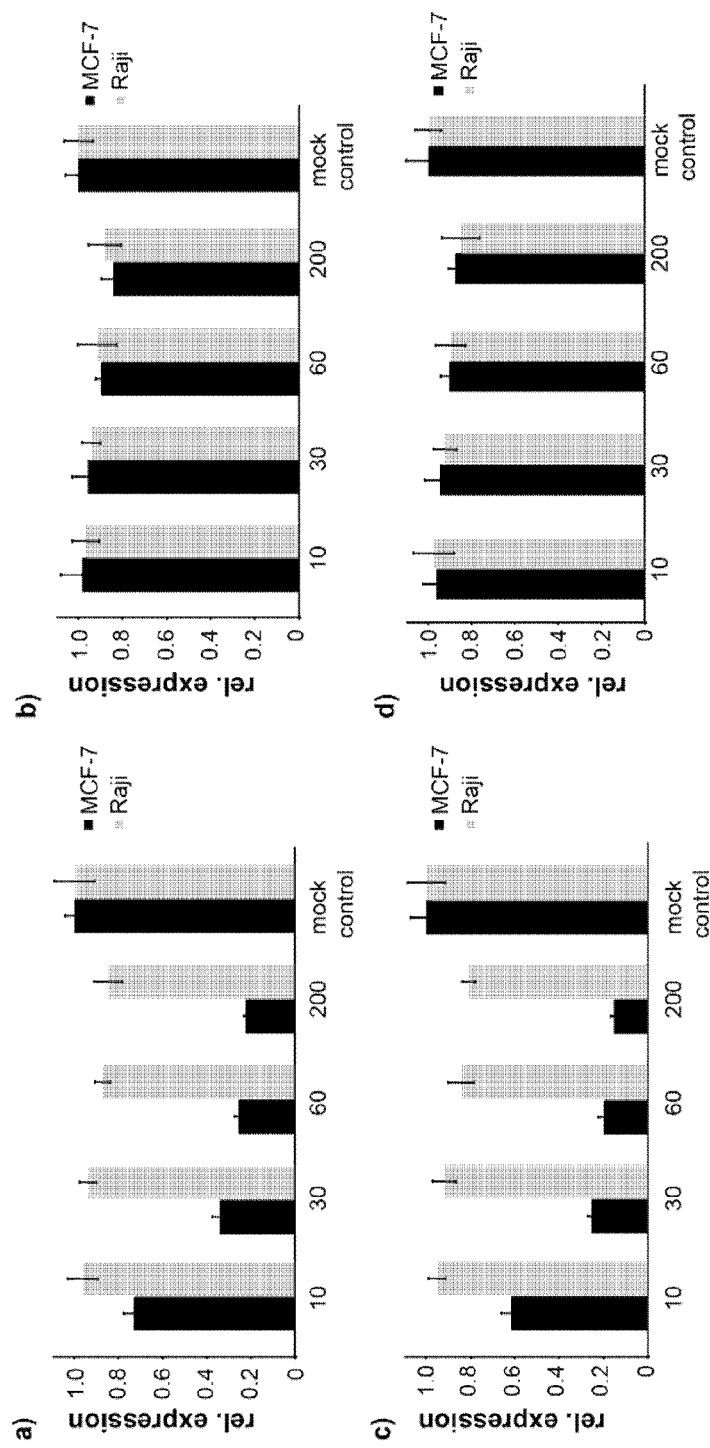

FIG. 3 The effect of A26-Streptavidin-siRNA complexes on MCF-7 and Raji cells gene expression. Cells were treated with complexes and UBR5 mRNA expression and Paip1 mRNA expression were detected by quantitative RT-PCR analysis in both control and target cells. Shown is the mRNA expression of Paip complex in FIG. 3a), control Paip complex in FIG. 3b), UBR complex in FIG. 3c) and control UBR complex in FIG. 3d).

Figure 4:
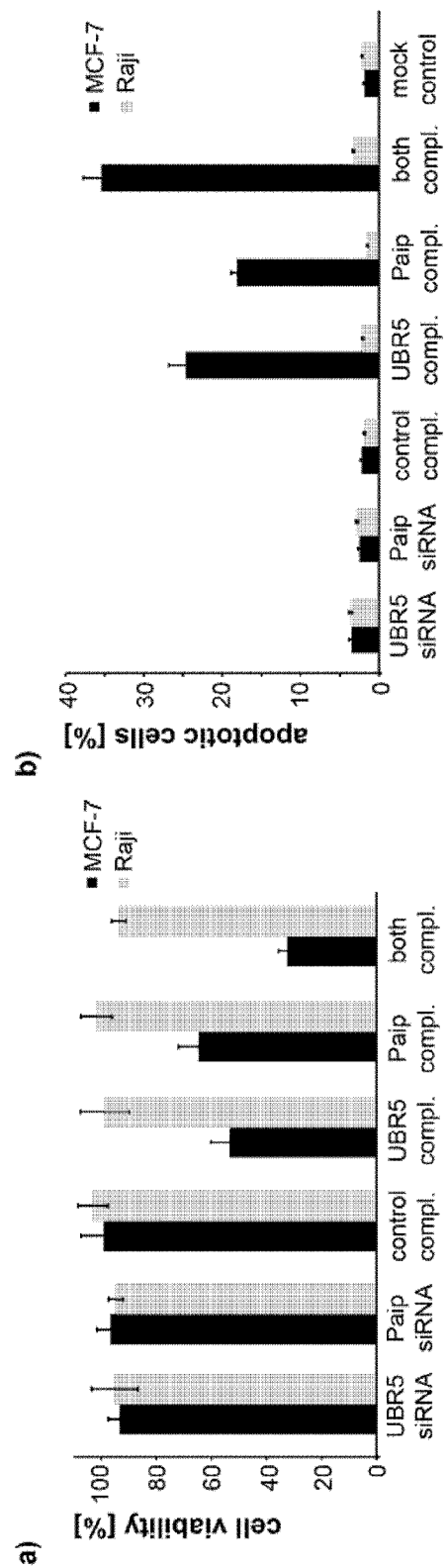

FIG. 4 The effect of naked siRNAs and A26-Streptavidin-siRNA complexes on control and target cells viability. The cells were treated with naked siRNAs and complexes and viability of cells was assessed by MTT assay as shown in FIG. 4a). The effect of naked siRNAs and A26-Streptavidin-siRNA complexes on apoptosis of MCF-7 cells and Raji cells is shown in FIG. 4b). The cells were treated with naked siRNAs and complexes and apoptotic cells were detected by FACS.

Figure 5:
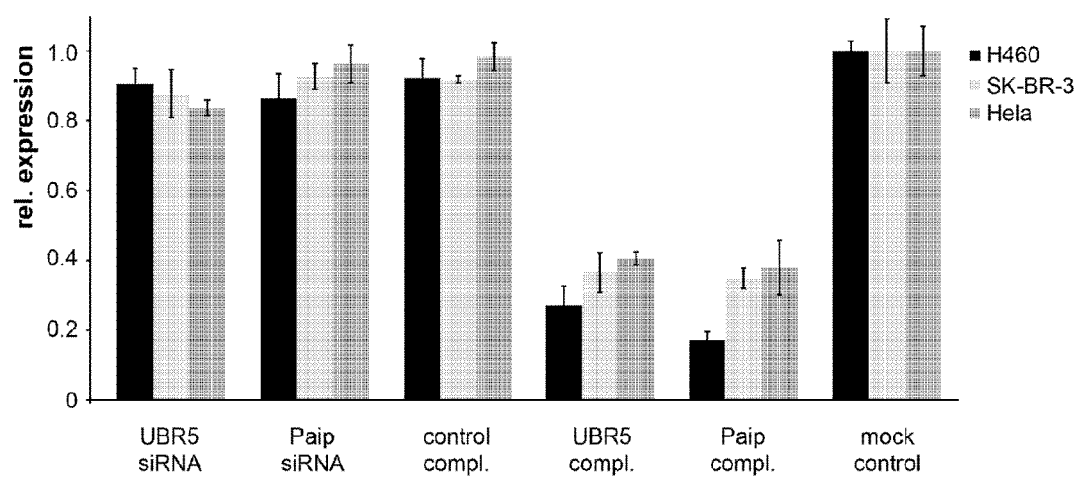

FIG. 5 The effect of A26-Streptavidin-siRNA complexes on H460, SK-BR-3, and HeLa cell gene expression. The cells were treated with the complexes and UBR5 mRNA expression and Paip1 mRNA expression were detected by quantitative RT-PCR analysis.

EXAMPLES

Cell Lines and Cell Culture

Cell lines MCF-7 (ATCC.HTB-22, human mammary gland adenocarcinoma), H460 (ATCC.HTB-177, human non-small lung carcinoma), A549 (ATCC. CCL-185, human non-small lung carcinoma), SK-BR-3 (ATCC.HTB-30, human mammary gland adenocarcinoma), Raji (ATCC.CCL-86, Human Burkitt's lymphoma), Jurkat (ATCC-TIB-152, human acute T cell leukemia), PC3 (ATCC. CRL-1435, human prostate adenocarcinoma), HPBMC (ECACC. 07073110, Human Peripheral blood Mononuclear Cells), HUVEC (ECACC. 06090720, Human Umbilical Vein Endothelial Cells) were grown in Roswell Park Memorial Institute 1640 medium (RPMI-1640, PAA). MEC-1 (DSMZ. ACC-497, Human chronic B cell leukemia) was grown in Iscove's Modified Dulbecco's Medium (IMDM, Invitrogen). HEK-293 (ATCC. CRL-1573, Human epithelial embryonic kidney) and NIH 3T3 (ECACC. 93061524, Mouse embryonic fibroblast) were grown in Dulbecco's modified Eagle medium (DMEM, PAA). Hela (ATCC.CCL-2.2, Human cervix adenocarcinoma) was grown in minimum essential medium (MEM, Invitrogen). All cell lines were supplemented with 10% heat inactivated fetal bovine serum (FBS, GIBCO) and 100 U/mL penicillin-streptomycin (Cellgro).

Statistics

Statistical tests were performed using the student's t-test. Data are means±SD, n=3 independent treatments. P values less than 0.05 were considered as significant; whereas P>0.05 means data are not significantly different.

Example 1

Selection of Aptamers

A human mammary gland adenocarcinoma cell line (MCF-7) was used as complex target during whole cell-SELEX selection. To deprive common cell-recognizing nucleic acid motifs a human lung carcinoma cell line, namely H460, was chosen. In this way the nucleic acids that recognize common cell structures may be eliminate, though limited to the extent possible. After incubating the DNA library with H460 cells, the supernatant was removed and added to MCF-7 cells. Subsequently, after washing the bound sequences were recovered and amplified.

The library contained a central randomized sequence of 43 nucleotides flanked by two 18 and 19 nucleotides PCR primer hybridization sites (5'-GCTGTGTGACTCCTG-CAA-43N-GCAGCTGTATCTTGTCTCC-3' (SEQ ID NO: 1), 5'-phosphorylated reverse primer (5'-Phos-GGAGA-CAAGATACAGCTGC-3'(SEQ ID NO: 26), and forward primer 5'-GCTGTGTGACTCCTGCAA-3' (SEQ ID NO: 27)) (Ella Biotech GmbH, Germany). All ATTO-labelled aptamer sequences were purchased from Microsynth (Switzerland). These ATTO-coupled sequences were used for determination of aptamers binding affinity, internalization assay and confocal imaging.

MCF-7 was used as the target cell line and H460 as the control cell line. The single-stranded DNA (ssDNA) library (1 nmol) dissolved in 100 μl washing buffer (1 L DPBS (Dulbecco's Phosphate-Buffered Saline, Gibco) with 5 mM $MgCl_2$), denatured by heating at 95° C. for 5 min, and cooled on ice for 10 min. The volume was filled up to 1000 μl with binding buffer (1 L DPBS, 1 g FBS, 5 mM $MgCl_2$ and 500 mg salmon sperm DNA). Then the library was incubated with H460 cells on a 100 mm diameter cell culture dish for 45 min at 37° C. Subsequently the library was incubated with MCF-7 cells on a 60 mm diameter cell for 45 min at 37° C. After incubation, the cells were washed twice with 1.5 ml of washing buffer (1 L DPBS, 5 mM $MgCl_2$) for 30 s. 500 μl of water was added and the cells were harvested using a cell scraper. The bound DNA sequences were eluted by heating at 95° C. for 4 min and the mixture was centrifuged at 12000 g to pellet the cell debris. The supernatant containing the ssDNA was recovered by phenol/chloroform extraction and ethanol precipitation and amplified by PCR (denaturing at 95° C. for 1 min, annealing at 64° C. for 1 min and extension at 72° C. for 90 s).

For each round of SELEX, the number of PCR cycles was optimized between 10 and 20. The PCR products were purified using nucleospin extract II kit (Macherey-Nagel) following the manufacturer's protocol. The single stranded DNA was generated by λ-exonuclease digest of the phosphorylated antisense strand and used for the next selection cycle. ssDNA was recovered by mixing of purified dsDNAs with a specific volume of λ-exonuclease enzyme (Fermentas, e.g., 2 μg of dsDNA with 1 μl of λ-exonuclease), and the mixture was adjusted to yield 1× λ-exonuclease reaction buffer conditions using 10× concentrated buffer stock. This mixture was immediately incubated at 37° C. for 35 min, followed by additional 10 min incubation at 80° C. to stop the enzymatic reaction. After digestion, ssDNA was purified using nucleospin extract II kit following the manufacturer's protocol. All product of the first round was used for the second round using the same procedure as described for first selection. For the third round, after heating pool at 95° C. and snap cooled, the library was used to perform negative selection using H460 cells.

The progress of the selection was monitored by radioactive assays, in which radioactively labelled ssDNA from different selection cycles was incubated with MCF-7 cells or H460 cells, respectively, and Cherenkov counting was applied to measure the amount of ssDNA retained on the cells after washing. In the counter selection, H460 cells were cultured in a 100 mm diameter cell culture. Similarly, cells were washed and incubated with pool. After incubation, the non-binding sequences in the incubation buffer were recovered and used for incubation with target cells using the same procedure as described for first selection. The entire selection process was repeated until significant enrichment was obtained for the MCF-7 cells (12 rounds) when analyzed by radioactive test. To acquire more specific and high affinity aptamers, the incubation time with target cells was decreased from 45 to 35 min as the number of selection rounds increased, the washing strength was increased by gradually increasing washing time (from 30 to 90 s), washing volume (from 1.5 to 3 ml) and washing cycles (from 2 to 3 times).

After 12 rounds of selection, the selected ssDNA pool was PCR-amplified with unlabeled primers, then cloned into *Escherichia coli* using the TOPO TA cloning kit (Invitrogen). Individual colonies were picked to extract the plasmids for sequencing using NucleoSpin® Plasmid kit (Macherey-Nagel). Cloned sequences were determined by GATC Biotech Company (Germany). Sequence alignment was performed with the sequence alignment program ClustalX2.0.10. Sequences were grouped into families and representative sequences from different families were selected as candidate aptamers for monoclonal testing.

As a result, sequence analysis provided the 12 candidate molecules having a nucleotide sequence as follows:

```
A28:
                                          (SEQ ID NO: 14)
5'-GCTGTGTGACTCCTGCAACAGGCCGGAGGGACTGGGGAGGT

GCGACGTTTACGTGTTCTCCGCAGCTGTATCTTGTCTCC-3',

A32:
                                          (SEQ ID NO: 15)
5'-GCTGTGTGACTCCTGCAACGTTGTTTGTTCGCTCCGGGCTG

TAGAGCCTCGAAGATGAGTTGCAGCTGTATCTTGTCTCC-3',

A26:
                                          (SEQ ID NO: 16)
5'-GCTGTGTGACTCCTGCAACCGGACTGCAGAGACCGTCTGTC

GGTGAACACTATTAGACGCGGCAGCTGTATCTTGTCTCC-3',

A33:
                                          (SEQ ID NO: 17)
5'-GCTGTGTGACTCCTGCAAGGCGGTACGCGTGTGGACAGAAG

TGACCGCCAAATAGCGCCTGGCAGCTGTATCTTGTCTCC-3',
```

```
-continued
A42:
                                          (SEQ ID NO: 18)
5'-GCTGTGTGACTCCTGCAACCAGACCGTAGGGGCTGTCTGTA

GAGGACGCTGACGCGCACGAGCAGCTGTATCTTGTCTCC-3',

A10:
                                          (SEQ ID NO: 19)
5'-GCTGTGTGACTCCTGCAACCTGTTCGGGCGCTAGCCTGATA

GAAGTGTGCGTTCAATGGTGGCAGCTGTATCTTGTCTCC-3',

A13:
                                          (SEQ ID NO: 20)
5'-GCTGTGTGACTCCTGCAACAGGTTGGGCTGATGGTGGGCAG

ACCGTAGGGTCCGTAATCCGGCAGCTGTATCTTGTCTCC-3',

A34:
                                          (SEQ ID NO: 21)
5'-GCTGTGTGACTCCTGCAAGGGGTACACGCGCATGCTCATCT

GGACCGGAGGGTTCCGGGGAGCAGCTGTATCTTGTCTCC-3',

A41:
                                          (SEQ ID NO: 22)
5'-GCTGTGTGACTCCTGCAACAAAGGGTCGGCGGACTGTTGAG

ACCACCGGCAGCGGGGCATTGCAGCTGTATCTTGTCTCC-3',

A1:
                                          (SEQ ID NO: 23)
5'-GCTGTGTGACTCCTGCAAGGGTACGGCATTGATTTGCTGCC

TTATTGGTGTTGGTGGGGGGCAGCTGTATCTTGTCTCC-3',

A5:
                                          (SEQ ID NO: 24)
5'-GCTGTGTGACTCCTGCAACATGCTTTATGTAACAGGCGGAG

GCCGTCCGTGGTACAGGTTCGCAGCTGTATCTTGTCTCC-3',

A2:
                                          (SEQ ID NO: 25)
5'-GCTGTGTGACTCCTGCAAGGAGGGGATCACACCGTATAGAC

TGCAGAGTTCTGTCGGTGTGGCAGCTGTATCTTGTCTCC-3'.
```

The sequence A28 (SEQ ID NO: 14) was the most dominant sequence.

Example 2

Determination of Cell Binding Against MCF-7 and H460 Cells

The binding of the aptamers obtained in Example 1 to the cell lines MCF-7, a human mammary gland adenocarcinoma cell line, and H460, a human non-small lung carcinoma cell line, was determined by radioactive interaction analysis.

To monitor the monoclonal aptamers for cell binding 5'-$^{32}$P-labeled ssDNA was prepared and incubated with the respective cells in 6-well plates for 40 min at 37° C. After removal of the supernatant, cells were washed three times with 1.5 ml washing buffer. Bound DNA was recovered by harvesting the cells and re-suspension in 1.5 ml washing buffer. In case of suspension cells supernatant and wash fractions were collected by centrifugation at 200 g for 4 min. The amount of radioactive labelled DNA in every fraction was determined by Cherenkov scintillation counting.

The FIG. 1 illustrates the results of the screening of the selection rounds 1 ("1") and 12 ("12") and the aptamers obtained in Example 1 against MCF-7 in FIG. 1a) and H460 in FIG. 1b). As can be taken from the figures, the aptamers A28, A32, A26, A42, A42, A13, A33 and A34 show good binding to MCF-7 cells (FIG. 1a) and H460 cells (FIG. 1b), while the sequences A1, A2, and A5 show lower binding. A comparison of the FIGS. 1a) and 1b) shows that no sequence was found to exclusively recognize MCF-7 cells.

Example 3

Determination of Binding to Further Cancer Types

The recognition of the selected aptamers was tested on the following cell lines human lung cancer cell line (A549), human cervical cancer cell line (Hela), human breast cancer cell line (SK-BR-3), transformed but non-tumour human embryonic Kidney cell line (HEK) and transformed but non-tumour mouse embryonic fibroblast cell line (3T3), as described in Example 2. As a control the starting pool (library) was used.

The aptamers A26, A28 and A32 showed stronger signals on cervix carcinoma cell line (Hela), lung cancer cell line (A549), and breast cancer cell line (SK-BR-3) compared to the transformed but non-tumour human embryonic Kidney cell line (HEK) and embryonic fibroblast cell line (3T3). Also, the aptamers A41, A42 and A13 showed strongest signals on Hela cells, and better binding was obtained with lung cancer cell line (A549), and breast cancer cell line (SK-BR-3) compared to the transformed but non-tumour cells, while the control showed only very low binding, demonstrating that contrary to the library the aptamers recognize a broad spectrum of tumour cells.

Example 4

Determination of Binding to Cancer Cells and Healthy Cells

For the aptamers A26, A28, A32 and A33, the determination of selectivity was further extended to other cell lines, including human burkitt's lymphoma cell line (Raji), human T cell lymphoblast cell line (Jurkat), human chronic B cell leukemia cell line (MEC1), human umbilical vein endothelial cell (HUVEC), and peripheral blood mononuclear cell line (PBMC) from healthy individuals. As described in Example 2, the aptamers and the starting pool (library) were 5'-$^{32}$P-labeled and incubated with different cell lines. The amount of ssDNA bound to the cells was measured using radioactive analysis.

FIG. 2 illustrates the results of the selectivity study to assess the recognition of the aptamers to different cell lines for the aptamers A33 (SEQ ID NO: 17), A26 (SEQ ID NO: 16), A28 (SEQ ID NO: 14) and A32 (SEQ ID NO: 15). As can be taken from the FIG. 3, the sequences A26, A28 and A32 showed stronger signals with cancer cells compared to those observed with non-cancer cells. The aptamers A26, A28 and A32 showed no significant interaction with these primary cells or cell lines (FIG. 4). This implies that the aptamers A26, A28 and A32 own a good specificity towards solid-tumour derived cancer cells.

Example 5

Determination of Apparent Affinities

Flow cytometry was used to determine the apparent affinities ($k_{app}$) of the aptamers for MCF-7 cells. Therefore, 5'-ATTO647N labelled variants of the aptamers were synthesized and their cell-binding behaviour was investigated by flow cytometry. Employing increasing concentrations of individual aptamers while keeping the amount of cells constant apparent affinities can be determined, thus providing means to rank the aptamers in respect of their concentration-dependent cell-recognition properties.

The binding affinity of aptamers was determined by incubating increasing concentrations of ATTO647N-labelled aptamers (0 to 900 nM) with MCF-7 cells in 12 well plates at 37° C. for 40 min. The cells were washed twice with 700 µl of washing buffer. The cells were scraped and suspended in 400 µl of washing buffer. The fluorescence intensity was determined by using a FACScan cytometer (FACS Canto II, BD) by counting 10000 events. The mean fluorescence intensity of cells labelled by aptamers was used to calculate the specific binding by subtracting the mean fluorescence intensity obtained for the non-specific binding control sequence (5'-GCTGTGTGACTCCTGCAAGAC-GGAC-CAGAGGGCGGAGAGCTTTGGCAGCTCTCGGCAT-CAAGCAGCTGTATCTTGTCTCC-3' (SEQ ID NO: 29)). The equilibrium apparent binding constants ($K_{app}$) of the aptamer-cell interaction were obtained by fitting the dependence of fluorescence intensity of specific binding on the concentration of the aptamers to the equation Y=B max X/($K_d$+X), using PrismGraphPad.

All aptamers revealed apparent affinities in the nanomolar range.

Example 6

Determination of Binding and Localisation of the Aptamers

The binding of the aptamers A26 (SEQ ID NO: 16) and A33 (SEQ ID NO: 17) to MCF-7 cells and the localisation of the aptamers was assessed by confocal microscopy. MCF-7 cells were seeded on glass coverslips in 6 well plates, and cultured overnight. The cells were carefully washed and then incubated with ATTO647N-labeled aptamers A26 and A33 and control sequence (A33sc) 5'-GCTGT-GTGACTCCTGCAAGACGGACCAGAGGGCGGA-GAGCTTTGGCAGCTCTCGGCATCA AGCAGCTGTATCTTGTCTCC-3' (SEQ ID NO: 29) at a final concentration of 100 nM for 2 h. After incubation, cells were carefully washed, fixed and stained with DAPI and Wheat germ agglutinin (WGA-488). DAPI staining was employed to visualize the nucleus. WGA-488 was used to stain the plasma membrane. The signal was detected by confocal microscopy (FV500-IX81 confocal microscope, Olympus America Inc., Melville, N.Y.), with 406oil immersion objective (NA=1.40, Olympus, Melville, N.Y.). Excitation wavelength and emission filters were as follows: PE, 488 nm laser line excitation, emission BP520; and Alexa Fluor 633 nm laser line excitation, emission LP650 filter.

The microscopy images reveal that the aptamers A26 and A33 were localized inside the tumour cells after 2 h incubation. These data qualify the aptamers A33 and A26 as molecular vehicle for cargo delivery into tumour cells.

Example 7

Determination of Cargo Delivery into MCF-7 Tumour Cells

For the targeted delivery into and treatment of MCF-7 cells, a ternary complex of A26-streptavidin and siRNA molecules was assembled. siRNA molecules either targeting Paip1 or UBR 5 mRNA were chosen. Paip1 regulates the activity of Poly (A) binding protein (PABP). PABP has an important role on both mRNA stability and translation in eukaryotic cells. Paip1 acts as a translational activator whereas Paip2 is a translational inhibitor in cultured mammalian cells. Paip2 competes with Paip1 for binding to PABP, inhibits binding of PABP to the mRNA poly (A) tail and, thus, prohibits translation in vitro and in vivo. Ubiquitin protein ligase E3 component n-recognin 5 (UBR5), also known as EDD1, plays an important role in ubiquitin conjugation. UBR5 targets Paip2, which is not bound to PABP, to the proteasome for degradation. Another role of UBR5 is the regulation of DNA damage responses. It has been demonstrated that UBR5 is highly expressed in several solid tumours, such as ovarian and breast cancer.

As a negative control against MCF-7, a human mammary gland adenocarcinoma cell line, the human burkitt's lymphoma cell line (Raji) was used.

A26-streptavidin-siRNA (siRNA against UBR5 or siRNA against Paip1) complexes, referred in the following to as UBR5 complex and Paip complex, respectively, were assembled and the influence of these complexes on tumour cell viability, induced apoptosis and level of the corresponding mRNA molecules of UBR5 and Paip1 was determined as follows.

7.1 siRNA Preparation siRNA sequences were designed according to software by Thermo Scientific (http://dharmacon.com/predesigned-siRna/search.aspx) and Invitrogen (https://rnaidesigner.invitrogen.com/rnaiexpress/). For Paip1 siRNA, the biotinylated (B) sense sequence with a disulfide linker (-s-s-) was 5'-B-s-s-GAAGAUGCUUGGAAGGAAAUU-3' (SEQ ID NO: 30) and the antisense sequence was 3'-UUCUUCUAC-GAACCUUCCUUU-5' (SEQ ID NO: 31). For UBR5 siRNA the biotinylated sense sequence with a disulfide linker was 5'-B-s-s-GCAAAUAGCAUAAGAGCAAUU-3' (SEQ ID NO: 32) and the antisense sequence was 3'-UUCGUUUAUCGUAUUCUCGUU-5' (SEQ ID NO: 33). The negative control siRNA biotinylated sense sequence with a disulfide linker was 5'-B-s-s-UUCUC-CGAACGUGUCACGU-3' (SEQ ID NO: 34) and the antisense sequence was 3'-ACGUGACACGUUCGGAGAA-5' (SEQ ID NO: 35). The sequences were purchased from Microsynth (Switzerland). The selected sequences were submitted to Blast (http://www.ncbi.nil.nih.gov/blast/) to make sure that the selected genes are targeted specifically.

7.2 Annealing of siRNA

To anneal the siRNA, 50 nM of each sense and antisense strands of siRNA were combined with annealing buffer (100 mM KOAc, 30 mM HEPES-KOH (pH 7.4) and 2 mM MgOAc). The solution was incubated for 2 min in a water bath at 95° C. and allowed to cool to room temperature within 50 min and was stored on ice until use.

7.3 Preparation of Nanocomplex System siRNA-A26 complexes were prepared by mixing 200 pmol double-stranded siRNA and 200 pmol biotin-A26 (Microsynth, Switzerland) conjugate with 100 pmol of streptavidin (Sigma) for 1 h. The complex was stored on ice until use.

7.4 Evaluation of Nanocomplex Formation

The formation of A26-Streptavidin-siRNA complex was assessed by 2% agarose gel electrophoresis. UBR5 siRNA, A26 aptamer and A26-Streptavidin-siRNA complex treated with dithiothreitol (DTT; Invitrogen) were loaded onto the gel. Gel electrophoresis was run at 100 V for 30 min using Tris-borate-EDTA buffer (TBE). The gel was stained using ethidium bromide and observed under a UV illuminator.

7.5 Aptamer-Mediated siRNA Transfection

MCF-7 cells and Raji cells were plated in 12-well plates. The following day the medium was exchanged and the cells were divided into four groups: 1) blank group, 2) control complex group wherein the concentration of siRNA was 10 nM, 30 nM, 60 nM or 200 nM, respectively, 3) UBR complex group wherein the concentration of siRNA was 10 nM, 30 nM, 60 nM or 200 nM, respectively, and 4) Paip complex group wherein the concentration of siRNA was 10 nM, 30 nM, 60 nM or 200 nM, respectively. The cells were incubated for 4 h with A26-Streptavidin-siRNA complexes, then the culture medium was removed and complete culture medium (Medium+10% FBS) was added. Cells were harvested 72 h after complex addition and gene expression inhibition was monitored by real-time PCR.

As a control complex (control compl.) A33sc-Streptavidin-siRNA having the sequence 5'-GCTGTGTGACTCCT-GCAAGACGGACCAGAGGGCGGAGAGCTTTGGCA-GCTCTCGGCATCA AGCAGCTGTATCTTGTCTCC-3' (SEQ ID NO: 29) was used, wherein the nucleotides of the $N_{43}$ part correspond to the nucleotides of SEQ ID NO: 8, but are arranged in a scrambled order.

FIG. 3 illustrates the effect of A26-Streptavidin-siRNA complexes on MCF-7 and Raji cells gene expression, wherein the mRNA expression of Paip complex is shown in FIG. 3a), control Paip complex in FIG. 3b), UBR complex in FIG. 3c) and control UBR complex in FIG. 3d). As can be taken from the FIGS. 3a) and 3c), the level of the corresponding mRNA molecules of Paip (FIG. 3a) and UBR5 (FIG. 3c) was concentration dependently down regulated upon incubation of MCF-7 cells with the respective complexes. Further, the escalating concentrations of 10 nM, 30 nM, 60 nM and 200 nM, respectively, of UBR complex and Paip complex showed that for both complexes cytotoxicity reaches a plateau by adding 60 nM and higher concentration of the complexes to MCF-7 cells. As can be taken from the FIGS. 3b) and 3d), replacing the aptamer A26 with a control non-binding ssDNA molecule (A33sc) had no effect on the mRNA levels. Likewise the levels of UBR5 and Paip mRNA were unaffected in Raji cells, which are not recognised by A26, as can be seen in the FIGS. 3a) to 3d).

7.6 MTT Assay

To monitor cell viability of MCF-7 and Raji cells upon treatment with the complexes or control complexes MTT assays were performed.

MCF-7 cells and Raji cells for control ($1.5 \times 10^4$) were seeded in 96-well plates. The following day old culture medium was replaced with fresh serum-free culture medium and cells were divided into five groups: 1) blank groups, 2) control complex group wherein the concentration of siRNA was 60 nM, 3) UBR complex group wherein the concentration of siRNA was 60 nM, 4) Paip complex group wherein the concentration of siRNA was 60 nM, 5) UBR complex and Paip complex group wherein the concentration of siRNA was 30 nM for each complex. 4 h after A26-Streptavidin-siRNA complex incubation with cells, culture medium was removed and complete culture medium was added to each well. Cells were incubated for 72 h. Then 20 µl MTT solution was added to each well and mixed. After 4 h of incubation, 200 µl DMSO was added to each well and absorbance was measured with a microplate reader (Biotrek, USA) at 545 nm. Each experimental condition was done in triplicate.

The FIG. 4a) illustrates the effect of naked siRNAs and A26-Streptavidin-siRNA complexes on control and target cells viability as assessed by MTT assay. As shown in FIG. 4a), the viability of MCF-7 and Raji cells upon treatment with UBR5 siRNA, Paip1 siRNA, or control complexes remains unchanged. In contrast, viability of cells incubated with UBR5 complex, Paip complex, or both complexes were significantly reduced. The viability of the control cell line (Raji) remained unchanged independently of the treatment procedure. Hence, treatment with UBR5 complex, Paip complex, or both complexes induced a significant reduction in cell proliferation in solid tumour cells, but not in control cells.

7.7 Determination of Cell Apoptosis

To determine whether the reduction in cell viability of MCF-7 cells caused by the UBR5 complex and the Paip complex was due to an increase in apoptosis, the number of apoptotic MCF-7 and Raji cells after treatment was evaluated by flow cytometry.

Annexin V-FITC apoptosis detection kit (Abcam) was used to study apoptosis. MCF-7 cells and Raji cells were plated in 12-well plates and were divided into the same five groups as in the MTT assay. The A26-Streptavidin-siRNA complexes treatments were as before. After 48 h, cells were collected and washed with PBS. Cells (~$5 \times 10^5$) were resuspended in 500 µl of binding buffer. 5 µl of annexin V-FITC and 5 µl of propidium iodide were added to each sample and incubated at room temperature for 5 min in dark. Apoptosis was determined by flow cytometry. Each group was assayed three times.

The effect of naked siRNAs and A26-Streptavidin-siRNA complexes on apoptosis of MCF-7 cells and Raji cells is shown in FIG. 4b). As shown in FIG. 4b), the amount of apoptotic MCF-7 cells (including early apoptotic cells and the late apoptotic cells) 48 h after treatment with UBR5 siRNA, Paip1 siRNA, or control complex was almost unchanged. However, incubation of cells with the UBR5 complex, Paip complex and both complexes clearly resulted in an induction of apoptosis. Again the amount of apoptotic Raji cells remained unaffected.

In summary, the results of the cargo delivery study demonstrate that the aptamer A26 is a suitable molecular vehicle for the targeted delivery of siRNA molecules into specific target cells.

Example 8

Determination of Cargo Delivery into Solid Tumour Cells

The targeted delivery of siRNA into tumour cells by a ternary complex of A26-streptavidin and siRNA molecules was repeated for other solid tumour cells, namely human non-small lung carcinoma cells (H460), a breast cancer cell line (SK-BR-3), and Hela (Human cervix adenocarcinoma) cells. The cells were treated with the complexes of A26-Streptavidin-siRNA complexes of UBR5 and Paip1, and UBR5 mRNA and Paip1 mRNA expression were detected by quantitative RT-PCR analysis, as described in Example 7.1 to 7.5. The H460, SK-BR-3, and Hela cells were treated with the complexes for 4 h, wherein 60 nM siRNA was used, respectively. After 4 h incubation of A26-Streptavidin-siRNA complexes with cells, the culture medium was removed and completed culture medium was added to each well. Cells were harvested 72 h after adding of the complexes and monitored for gene expression inhibition by real-time PCR.

FIG. 5 illustrates the effect of A26-Streptavidin-siRNA complexes on H460, SK-BR-3, and HeLa cell gene expression. As can be taken from the FIG. 5, the level of the corresponding mRNA molecules of Paip1 and UBR5 was down-regulated upon incubation of cells with the respective complexes.

The results demonstrate the aptamer A26 to be a suitable broad-spectrum aptamer vehicle for targeted delivery of siRNA molecules into solid tumour cells of different origin.

The invention claimed is:

1. An aptamer, wherein the aptamer comprises a nucleotide sequence (SEQ ID NO: 1) according to general formula (1) as given as follows or a pharmaceutically acceptable salt thereof:

5'-GCTGTGTGACTCCTGCAA-N43-GCAGCTG-TATCTTGTCTCC-3' (1) (SEQ ID NO: 1), wherein:

N43 is a nucleotide sequence selected from the group comprising:

5'-CCGGACTGCAGAGACCGTCTGTCGGT-GAACACTATTAGACGCG-3' (SEQ ID NO: 2),
5'-CGTTGTTTGTTCGCTCCGGGCTGTAGAGCCTC-GAAGATGAGTT-3' (SEQ ID NO: 3),
5'-CAGGCCGGAGGGACTGGGGAGGTGCGACGTT-TACGTGTTCTCC-3' (SEQ ID NO: 4),
5'-CCAGACCGTAGGGGCTGTCTGTAGAG-GACGCTGACGCGCACGA-3' (SEQ ID NO: 5),
5'-CCTGTTCGGGCGCTAGCCTGATAGAAGTGT-GCGTTCAATGGTG-3' (SEQ ID NO: 6),
5'-CAGGTTGGGCTGATGGTGGGCAGACCG-TAGGGTCCGTAATCCG-3' (SEQ ID NO: 7),
5'-GGCGGTACGCGTGTGGACAGAAGTGACCGC-CAAATAGCGCCTG-3' (SEQ ID NO: 8),
5'-GGGGTACACGCGCATGCTCATCTGGACCG-GAGGGTTCCGGGGA-3' (SEQ ID NO: 9),
5'-CAAAGGGTCGGCGGACTGTTGAGACCACCG-GCAGCGGGGCATT-3' (SEQ ID NO: 10),
5'-GGGTACGGCATTGATTTGCTGCCTTATTGGTGT-TGGTGGGGGG-3' (SEQ ID NO: 11),
5'-CATGCTTTATGTAACAGGCGGAGGCCGTC-CGTGGTACAGGTTC-3' (SEQ ID NO: 12) and
5'-GGAGGGGATCACACCGTATAGACTGCAGAGT-TCTGTCGGTGTG-3' (SEQ ID NO: 13), or wherein the aptamer comprises a nucleotide sequence selected from the group comprising SEQ ID NOs: 2 to 13 or a pharmaceutically acceptable salt thereof.

2. The aptamer according to claim 1, wherein the nucleotide sequence is selected from the group comprising:

```
                                                  (SEQ ID NO: 14)
5'-GCTGTGTGACTCCTGCAACAGGCCGGAGGGACTGGGGAGGT

GCGACGTTTACGTGTTCTCCGCAGCTGTATCTTGTCTCC-3', (SEQ ID NO: 15)
5'-GCTGTGTGACTCCTGCAACGTTGTTTGTTCGCTCCGGGCTG

TAGAGCCTCGAAGATGAGTTGCAGCTGTATCTTGTCTCC-3',
```

```
                                                  (SEQ ID NO: 16)
5'-GCTGTGTGACTCCTGCAACCGGACTGCAGAGACCGTCTGTC

GGTGAACACTATTAGACGCGGCAGCTGTATCTTGTCTCC-3',
and (SEQ ID NO: 17)
5'-GCTGTGTGACTCCTGCAAGGCGGTACGCGTGTGGACAGAAG

TGACCGCCAAATAGCGCCTGGCAGCTGTATCTTGTCTCC-3'.
```

3. The aptamer according to claim 1, wherein the aptamer comprises the nucleotide sequence SEQ ID NO: 16.

4. The aptamer according to claim 1, for use as a medicament or a diagnostic reagent.

5. The aptamer according to claim 1, for use in the diagnosis and treatment of cancer, particularly solid tumours.

6. The aptamer according to claim 5, wherein the solid tumours are selected from the group comprising mammary gland adenocarcinoma, breast cancer, lung cancer, cervix cancer and pancreas carcinoma.

7. The aptamer according to claim 4, wherein the aptamer comprises the nucleotide sequence SEQ ID NO: 16.

8. A composition comprising an aptamer according to claim 1.

9. A pharmaceutical composition comprising as an active ingredient an aptamer according to claim 1.

10. The composition according to claim 8 for use in the detection or diagnosis, or the treatment of cancer, particularly solid tumours.

11. A solid tumour-specific drug delivery composition comprising an aptamer according to claim 1, and an anti-cancer agent such as a toxin, an anti-cancer growth inhibitor gene, an antagomir, siRNA, or combinations thereof.

12. An in vitro method of detecting or diagnosing a predisposition of solid tumours, the method comprising the steps of bringing an aptamer according to claim 1 into contact with a cell, tissue or sample obtained from a subject, and detecting the binding of an aptamer to the cell, tissue, or sample.

13. A method of treating solid tumours the method comprising the step of administering to a subject a therapeutically effective amount of an aptamer according to claim 1 coupled with an anti-cancer agent such as a toxin, an anti-cancer growth inhibitor gene, an antagomir, siRNA, or combinations thereof.

* * * * *